April 26, 1955 T. J. CURTIS ET AL Plant Pat. 1,386
DAHLIA PLANT
Filed Dec. 11, 1953
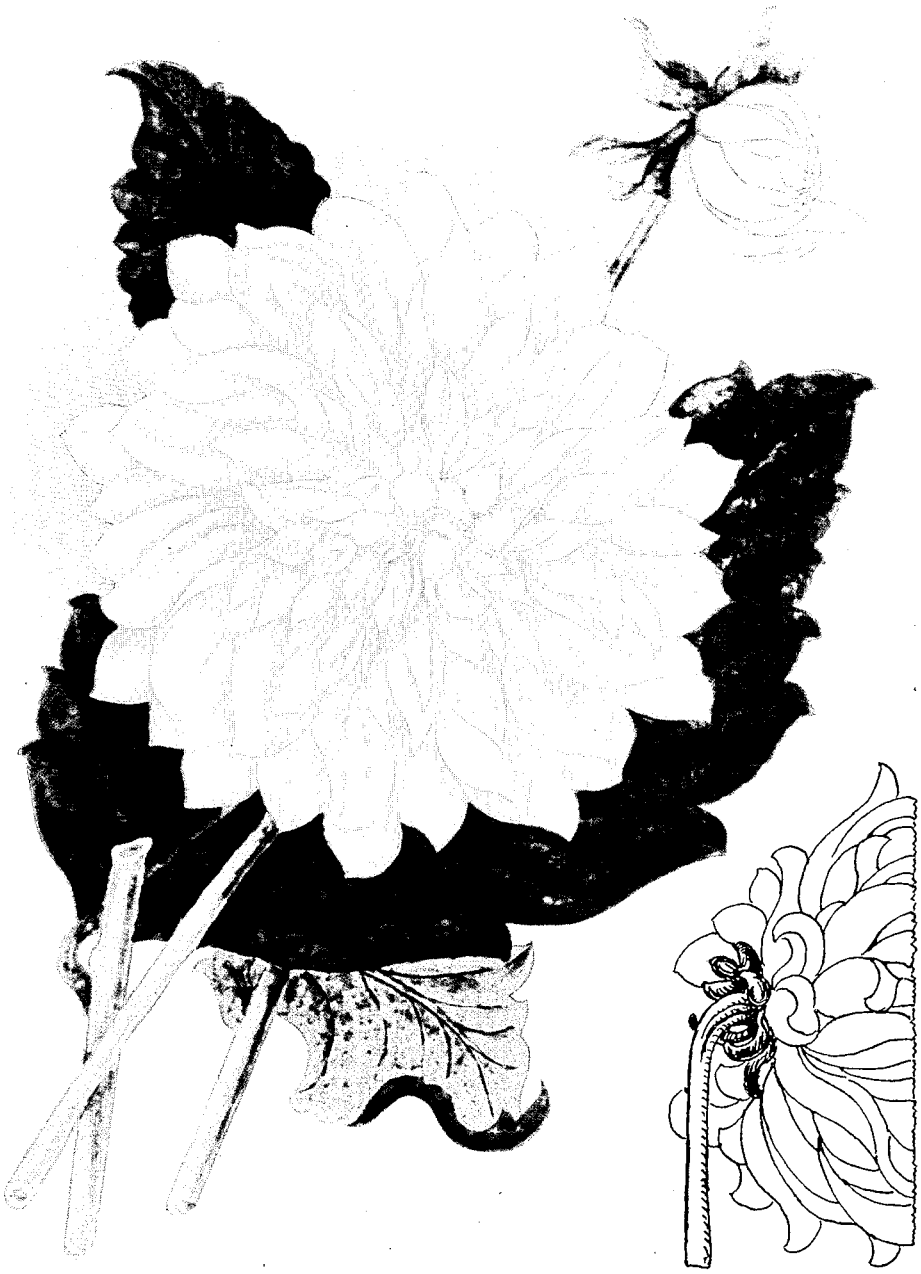
WITNESS
Addison E. Avery
INVENTORS,
THOMAS J. CURTIS & IVOR WILLIAMS,
by Rummler Rummler & Snow,
ATTYS.

United States Patent Office

Plant Pat. 1,386
Patented Apr. 26, 1955

1,386

DAHLIA PLANT

Thomas Johnstone Curtis and Ivor Williams, Lake Forest, Ill., assignors to Edison Dick, Lake Forest, Ill.

Application December 11, 1953, Serial No. 397,808

1 Claim. (Cl. 47—60)

This invention relates to a new and distinct variety of dahlia plant of the decorative type, characterized by the size and color of its blooms and the form and curl of its petals.

The variety originated as a seedling resulting from a series of adjacent plantings of selected varieties of dahlia plants grown by us at Lake Forest, Illinois, in 1947. This plant was discovered by us in 1947 and was subsequently reproduced asexually by us in the garden of Mr. Edison Dick at Lake Forest, Illinois, since 1951 from cuttings and roots and has been found to remain true to form and color characteristics.

The novelty of the plant resides in the color and form of its blooms which are very large and pure white in external appearance. The petalage is very double and the bloom is semi-spherical in general contour, slightly depressed at the center and stands singly at the side of the axis of its stem rather than in line therewith, the stem being bent at a right angle closely adjacent the flower.

The accompanying drawing, in its main view, shows in a front view the color and form of the bloom and foliage, the arrangement and shape of the petals and the general appearance of the bud. The second view is a pen and ink sketch showing the disposition of the bloom on its stem. The petals have plicate veins that are of substantially the same pure white color as the body of the petals and visible only on close inspection. The inner petals have a faint lemon tint at their base which is scarcely visible in the open flower and then only on close inspection in the depths of the flower between petals where the innermost petals curl inward hiding the genital organs.

The color designations according to "A Dictionary of Color by Maerz and Paul" are as follows:

| | Plate | Ltr. | No. |
|---|---|---|---|
| Flower: | | | |
| Inner petals have pale lemon yellow tint near the base shading rapidly outward to pure white in the main body portion of the petals | 9 | K | 1 |
| Bud: | | | |
| Yellow-green turning white as the bud develops | 19 | L | 1 |
| Leaf: | | | |
| Main leaf—upper side | 23 | L | 8 |
| Under side | 21 | O | 6 |

A specific description of the plant is as follows:

Origin: Seedling.
Parentage: Unknown.
Flower: Recurrent.
- *Blooms.*—Profusely midseason to late fall.
- *Size.*—8 in. to 9 in. 7 in. to 8 in. as season wanes.
- *Borne.*—Singly.
- *Shape.*—Informal round and high in general contour with slightly depressed center.
- *Shape.*—Informal round and high in general contour with slightly depressed center.
- *Petalage.*—Form—oblanceolate. Inner petals at center longitudinally curled over the sexual organs which are completely hidden except in final stages of bloom. Arrangement—loose, free and fluffy. Color—outer petals, white; inside petals, white with faint yellow tint at base; reverse side, same. In intermediate layers the rays have lateral portions curled inward and overlapping, such curling being less in varying degrees in successive layers until the rays of outer layers are quite flat. Discoloration—none. Appearance—satiny.
- *Affected by wet or hot weather.*—No.
- *Persistence.*—Hang on and dry.
- *Lasting quality.*—Good on plant and as a cut flower.

Bud:
- *Form.*—Globular.
- *Color.*—Yellow-green turning to white as petals divide.
- *Sepals.*—Stand out from bud.
- *Calyx.*—Size—broad; does not split. Aspect—smooth.

Plant:
- *Form.*—Bush.
- *Height.*—6 to 7 feet.
- *Growth.*—Strong, vigorous and branching.

Foliage: Abundant.
- *Size of leaf.*—Large.
- *Texture.*—Leathery.
- *Color.*—Upper side, dark green. Under side, lighter green.

This new variety of dahlia is distinguished from other varieties by the predominant whiteness of its petals, the overlapping lateral curling of its petals near the center which is of less degree progressively in outer layers and flattens out in the outermost layers, the facing of the flower on the side rather than upward on the stem, the large deep green leaves which form a contrasting background for the very white blooms, and the lasting quality of the blooms when cut.

We claim:

The new and distinct variety of dahlia plant, substantially as shown and described, having large blooms standing at right angle to their stems, with very double petalage, with a central group curled longitudinally completely covering the sexual organs, with adjacent rows of inner petals curled both longitudinally and laterally to open-ended tubular form, with successive intermediate layers of rays of successively less curvature and outer layers almost flat, the color of the blooms being dominantly pure white.

No references cited.